US00PP23288P2

(12) United States Plant Patent
Richer

(10) Patent No.: US PP23,288 P2
(45) Date of Patent: Jan. 1, 2013

(54) SHRUB ROSE PLANT NAMED 'NAVY LADY'

(50) Latin Name: *Rosa hybrida*
Varietal Denomination: Navy Lady

(75) Inventor: Claude Richer, Saint-Félix-de-Valois (CA)

(73) Assignee: Her Majesty the Queen in Right of Canada as Represented by The Minister of Agriculture and Agrifoods, Alberta (CA)

( * ) Notice: Subject to any disclaimer, the term of this patent is extended or adjusted under 35 U.S.C. 154(b) by 440 days.

(21) Appl. No.: 12/799,312

(22) Filed: Apr. 22, 2010

(51) Int. Cl.
*A01H 5/00* (2006.01)

(52) U.S. Cl. ..... Plt./108

(58) Field of Classification Search ..... Plt./108
See application file for complete search history.

(56) References Cited

U.S. PATENT DOCUMENTS

PP11,118 P * 11/1999 Andersen et al. ..... Plt./181

OTHER PUBLICATIONS

UPOV ROM GTITM Computer Database, GTI Jouve Retrieval Software Citation for 'Navy Lady' Accessed Sep. 28, 2011.*
Anonymous. "The Canadian Naval Centennial Rose AC Navy Lady" accessed via Internet at wrcns on Oct. 1, 2011.*
Anonymous. "AC Navy Lady" available at HelpMeFind.com accessed Oct. 1, 2011.*

* cited by examiner

*Primary Examiner* — Wendy C Haas
(74) *Attorney, Agent, or Firm* — Penny J. Aguirre

(57) ABSTRACT

A new cultivar of shrub rose, 'Navy Lady', characterized by its small, compact, and uniform plant habit, its lightly fragrant semi-double flowers that are deep red in color opening from buds that are very dark red in color with its petals exhibiting a velvety texture, its repeat blooming habit, its medium to dark green semi-glossy foliage with good resistance to powdery mildew and rust, its vigorous growth habit, its ability to be readily propagated on its own roots, and its cold hardiness at least to U.S.D.A. Zone 4.

2 Drawing Sheets

Botanical classification: *Rosa hybrida.*
Variety denomination: 'Navy Lady'.

BACKGROUND OF THE INVENTION

The present invention relates to a new and distinct cultivar of *Rosa hybrida*. The new cultivar will be referred to hereafter by its cultivar name, 'Navy Lady'. 'Navy Lady' is a new cultivar of shrub rose grown for use as a landscape shrub.

The new cultivar of shrub rose is a selection from a controlled breeding program conducted by the inventor in Saint-Jean-sur-Richelieu, Quebec, Canada with a focus to create rose cultivars with greater hardiness and disease resistance, improved plant form and length of flowering period, and unique flower colors.

The new variety of shrub rose, 'Navy Lady' was selected by the Inventor among seedlings derived from a cross made in Saint-Jean-sur-Richelieu, Quebec, Canada in 2003 between the female parent, 'Fourth of July' (U.S. Plant Pat. No. 11,518) and the male parent, 'Astrid Lindgren' (not patented). 'Navy Lady', designated as seedling no. ST03H003-02, was planted in the field in 2004, and selected and advanced to additional trials until 2008, when it was selected by the Inventor as a single unique plant with distinct characteristics.

The new cultivar was first asexually propagated by the Inventor by softwood cuttings in Saint-Jean-sur-Richelieu, Quebec, Canada in 2004. Asexual propagation determined that the characteristics of this cultivar are stable and are reproduced true to type in successive generations.

SUMMARY OF THE INVENTION

The following traits have been repeatedly observed and represent the characteristics of the new rose as observed for a period of four years in Quebec, Canada. These attributes in combination distinguish 'Navy Lady' as a unique cultivar of shrub rose.

1. 'Navy Lady' exhibits semi-double flowers that are dark red in color and emerge from flower buds that are very dark red in color.
2. 'Navy Lady' exhibits flower petals with a velvety texture.
3. 'Navy Lady' exhibits flowers with a light rose scent.
4. 'Navy Lady' exhibits medium to dark green, semi-glossy foliage.
5. 'Navy Lady' exhibits a repeat blooming habit, commencing in mid June and repeating for up to 12 weeks in Quebec, Canada.
6. 'Navy Lady' is a small shrub with uniformity in form.
7. 'Navy Lady' has shown good resistance to powdery mildew (*Sphaerotheca pannosa* var. *rosa*) and rust (*Phragmidium* spp.)
8. 'Navy Lady' is cold hardy at least to U.S.D.A. Zone 4.
9. 'Navy Lady' is a vigorous grower and readily propagated by softwood cuttings and grown on its own roots.

The new cultivar of shrub rose can be readily distinguished from its parents. The female parent, 'Fourth of July', differs from 'Navy Lady' in having red and white flowers, a climbing habit, and with less cold hardiness. The male parent, 'Astrid Lindgren', differs from 'Navy Lady' in having pink double flowers with greater fragrance. 'Navy Lady' can also be compared to 'Champlain' (not patented), which is similar to 'Navy Lady' in plant hardiness and in having flowers that are red in color. 'Champlain' differs from 'Navy Lady' in having greater susceptibility to powdery mildew, fully double flowers, lighter red flowers and flower buds, a taller stature, and a recurrent blooming habit.

BRIEF DESCRIPTION OF THE DRAWING

The accompanying colored photographs illustrate the overall appearance and distinct characteristics of the new shrub rose, 'Navy Lady'. The photographs were taken of one year-old plants (from a bud graft) of 'Navy Lady' as grown outdoors in St. Catherines, Ontario, Canada.

The photograph in FIG. 1 provides a view of fully mature flowers, the photographs in FIG. 2 provides a view of a row of plants in full bloom and the photographs in FIG. 3 and FIG. 4 provide a view of the developing flowers and flower buds. The white spots and droplets are due to morning dew. The colors in the photographs are as close as possible with digital photography techniques available, the color values cited in the detailed botanical description accurately describe the colors of the new shrub rose.

DETAILED BOTANICAL DESCRIPTION

Figure 1:
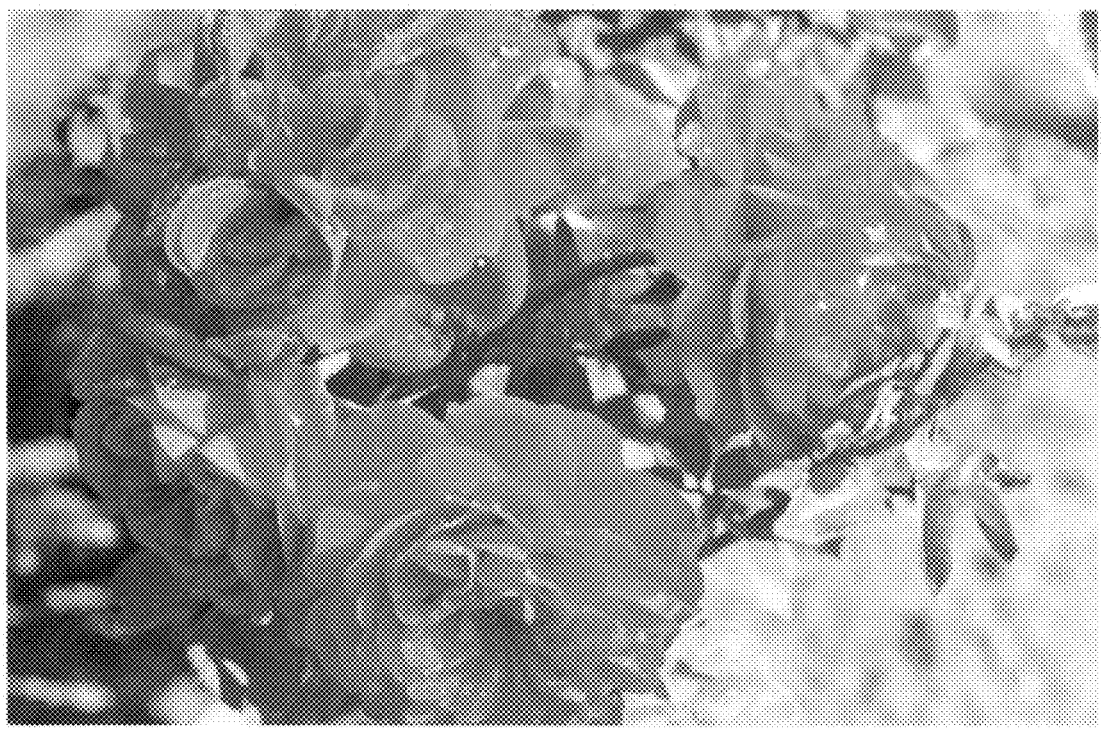
Figure 2:
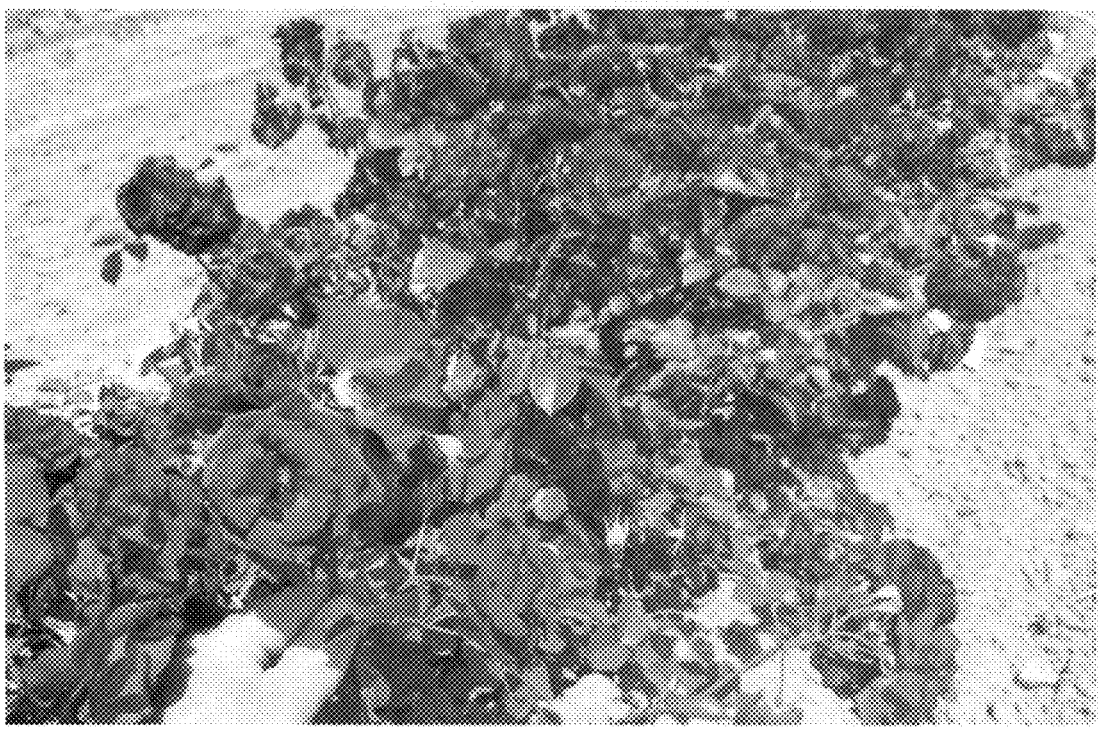
Figure 3:
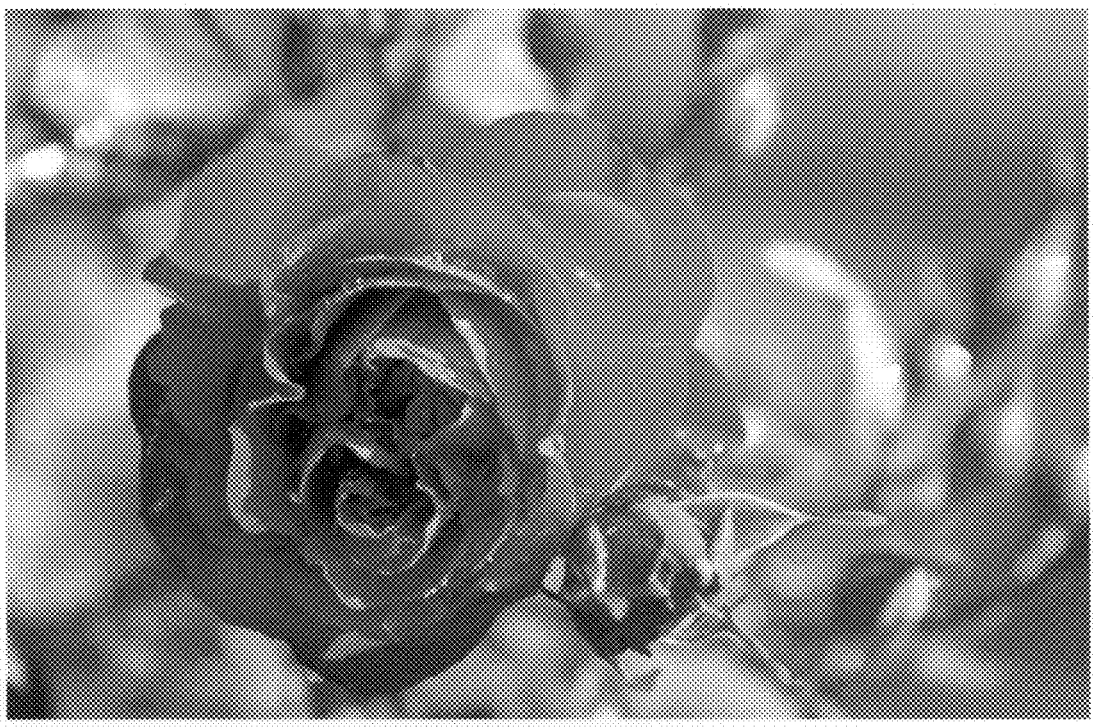
Figure 4:
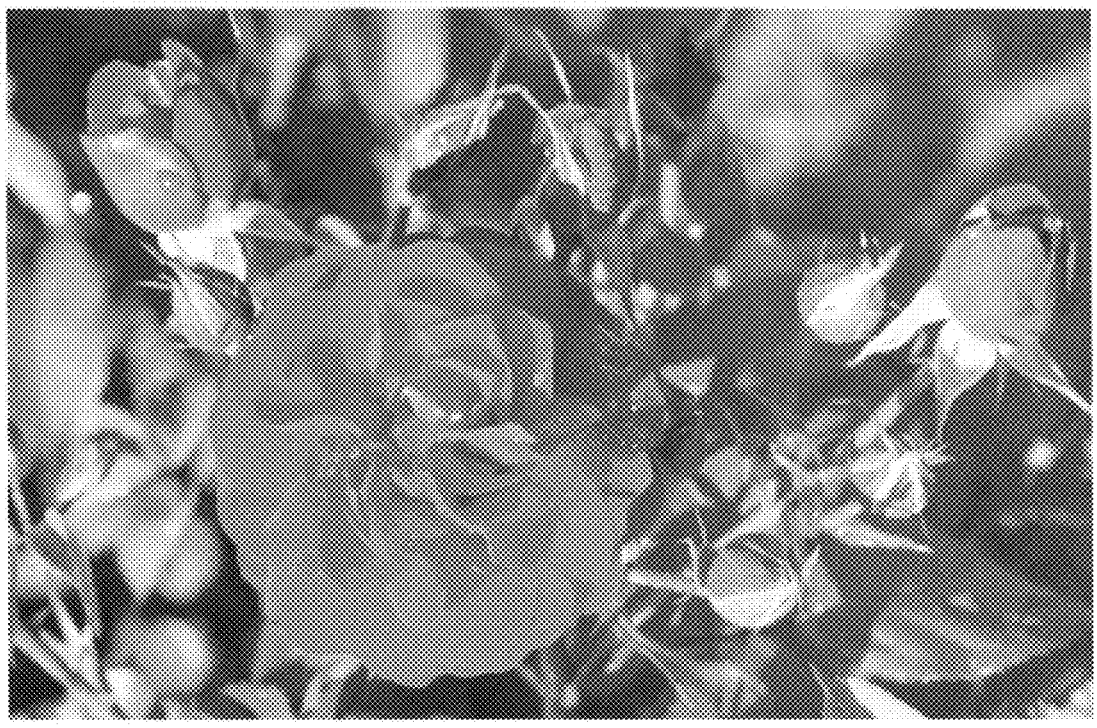

The following is a detailed description of two year-old plants the new cultivar as grown outdoors in a field plot in Saint-Jean-sur-Richelieu, Quebec, Canada. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming habit*.—Repeat blooming for up to 12 weeks, commencing in June in Quebec, Canada.

*Plant habit*.—Compact, relative small, rounded but wider than tall, uniform.

*Height and spread*.—50 to 65 cm in height and about 1 m in spread.

*Cold hardiness*.—At least to U.S.D.A. Zone 4.

*Diseases and pests*.—Good resistance to powdery mildew (*Sphaerotheca pannosa* var. *rosa*) and rust (*Phragmidium* spp.).

*Propagation*.—Easily propagated, softwood stem cuttings, own roots.

*Growth*.—Rapid and vigorous.

Branch description:

*Stem color*.—Young; 143C, maturing; 138B with sparse spots of N199B, mature wood; a blend of 200A, 200B, and N199B.

*Stem surface*.—Young; glabrous and slightly glaucous, mature; glabrous, adult wood; finely barked.

*Branching*.—1 to 2 lateral branches.

*Stem size*.—Average of 6 mm in width, up to 52 cm in length.

*Thorns*.—Shape triangular, aspect outward, base oval, average of 4 in number per 6 stem 6 cm in length, average of 4 mm in length with a base 4 mm in length and 2 mm in width, 165A in color.

Foliage description:

*Leaves*.—Division is odd-pinnate, arrangement is alternate, average of 8 cm in length and 5.6 cm in width, internode length is an average of 3 cm.

*Leaflets*.—5 to 7, average of 3 cm in length and 2.8 cm in width, broadly elliptic to ovate in shape, rounded base, cuspidate to acuminate apex, serrated margins, color emerging leaves upper surface and lower surface; 144A with fine margin of 183A, color young leaves upper surface; 137B suffused with N186C with margins N186C, color young leaves lower surface; 138B suffused with N186C with margins N186C, color mature leaves upper surface; N137B, color mature leaves lower surface; between 147B and 147C, pinnately veined (not conspicuous) with veins 153D at base of leaves on upper and lower surface, surface glabrous and glossy on upper surface and glabrous and dull on lower surface.

*Rachis*.—Average of 4.5 cm in length and 1.2 mm in diameter, color of upper surface and lower surface 146C and heavily suffused with 183C, surface is glabrous on upper and lower surface.

*Stipules*.—Aspect outward with auricle facing outward, adnate to petiole, average of 1.2 cm in length and 5 mm in width, color upper and lower surface; 144B and suffused with 183C, surface is glabrous on upper surface and lower surface.

*Petioles and petiolules*.—Petioles; an average of 2 cm in length and 1.5 mm in diameter, petiolules; an average of 2 mm in length and 1 mm in diameter, petioles and petiolules; color on young leaves 146C on lower surface and 183C on upper surface, color on mature leaves both surfaces 146C and lightly suffused on margins with 183C, surface glabrous on upper and lower surfaces.

Inflorescence description:

*Inflorescence type*.—Typically corymbs of 3 flowers of semi-double, rosette formed flowers.

*Flower number*.—Average of 9 per lateral stem.

*Flower fragrance*.—Light rose scent.

*Flower longevity*.—About 10 days, depending on temperature and sunlight exposure.

*Flower type*.—Semi-double, irregularly rounded in form with flattened convex on upper part of flower.

*Flower size*.—Average of 6.5 cm in diameter and 2.7 cm in depth.

*Peduncles*.—Round in shape, average of 2.5 cm in length and 1.8 mm in diameter, sparsely pubescent surface, 144B and lightly suffused with 183B in color.

*Bracts*.—None observed.

*Flower buds*.—Ovate in shape, an average of 2.5 cm in length and 2.8 cm in width prior to opening, color 46A.

*Sepals*.—5, triangular in shape, margin primarily entire with 2 to 3 very fine leafy appendages about 3 mm in length, color of upper and lower surface a blend of N144A and 144A with the lower surface suffused with 59A, average of 1.8 cm in length and 6 mm in width, acuminate apex, truncate base, reflexed to stem in aspect, puberulent surface.

*Petals*.—An average of 24 per flower, drop readily and cleanly, obcordate in shape, upper surface is velvety, lower surface is glabrous and waxy, margin entire with notch at apex, base cuneate, apex is rounded with small notch, average of 2.9 cm in length and 2.8 cm in width, color: opening and fully open flowers upper and lower surface; 46A (slightly redder) with base 58B and very tip of base 155A, fading flowers upper and lower surface; 53A (slightly redder).

*Receptacle*.—Average of 6 mm in diameter and 2 mm in depth when flower is fully open, donut shaped, waxy surface, 145B in color.

*Pistils*.—About 25 per flower, stigma is an average of 0.5 mm in length and 1 mm in width and 161A in color, style is an average of 2 mm in length and 63B in color, no petaloid pistils, ovary is cone-shaped, 8 mm in length and 6 mm in width and 145B and slightly suffused with 59A in color.

*Stamens*.—About 45, filaments are about 7 mm in length and 58D in color, anthers are an average of 1.2 mm in length, an average of 0.7 mm in width and 166A in color, pollen is abundant in quantity and 20B in color.

*Hips*.—Urn-shaped, an average of 1.5 cm in length and 1.2 cm diameter, surface is glabrous and shiny, color is a blend of 144B and 146C, seeds; average of 3 (fully developed) per hip, an average of 6 mm in length and 4 in diameter, surface is glossy.

It is claimed:

1. A new and distinct cultivar of shrub rose plant named 'Navy Lady' as herein illustrated and described.

* * * * *